United States Patent
Roselli et al.

(10) Patent No.: US 9,730,691 B2
(45) Date of Patent: Aug. 15, 2017

(54) ENDOVASCULAR STAPLE CLIP AND STAPLER

(71) Applicant: THE CLEVELAND CLINIC FOUNDATION, Cleveland, OH (US)

(72) Inventors: Eric E. Roselli, Rocky River, OH (US); Ryan S. Klatte, Fairview Park, OH (US); Mark S. Lobosky, Chardon, OH (US); Mark Howell, Cleveland, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 649 days.

(21) Appl. No.: 14/178,981

(22) Filed: Feb. 12, 2014

(65) Prior Publication Data

US 2014/0224858 A1     Aug. 14, 2014

Related U.S. Application Data

(60) Provisional application No. 61/763,604, filed on Feb. 12, 2013.

(51) Int. Cl.
| | | |
|---|---|---|
| A61B 17/122 | (2006.01) | |
| A61B 17/064 | (2006.01) | |
| A61B 17/068 | (2006.01) | |

(52) U.S. Cl.
CPC ...... *A61B 17/0644* (2013.01); *A61B 17/0682* (2013.01); *A61B 2017/0641* (2013.01)

(58) Field of Classification Search
CPC ........................... A61B 17/0644; A61B 17/083

USPC ......... 227/901, 902; 606/142, 143, 151, 219
See application file for complete search history.

(56) References Cited

U.S. PATENT DOCUMENTS

| | | | | |
|---|---|---|---|---|
| 6,322,580 | B1* | 11/2001 | Kanner | A61B 17/0057 606/213 |
| 6,387,105 | B1* | 5/2002 | Gifford, III | A61B 17/064 227/179.1 |
| 7,182,763 | B2* | 2/2007 | Nardella | A61B 17/0057 606/41 |
| 2003/0032981 | A1* | 2/2003 | Kanner | A61B 17/0057 606/219 |
| 2013/0274646 | A1* | 10/2013 | Paris | A61M 27/002 604/8 |

* cited by examiner

*Primary Examiner* — Hemant M Desai
*Assistant Examiner* — Eyamindae Jallow
(74) *Attorney, Agent, or Firm* — Tarolli, Sundheim, Coveil & Tummino LLP

(57) ABSTRACT

A staple clip for providing an attachment function in a surgical procedure is described. A center hub has a center hub aperture. The center hub defines a lateral hub plane. A plurality of joining legs each has an inner leg end attached to the center hub and an outer foot defining a lateral foot plane. The inner leg end and outer foot are separated along the leg by an elongate leg body extending laterally outward and longitudinally downward from the center hub. A plurality of lobe pads are attached to the center hub and lie substantially within the lateral hub plane. The inner leg ends and lobe pads alternate with each other around a periphery of the center hub.

2 Claims, 8 Drawing Sheets

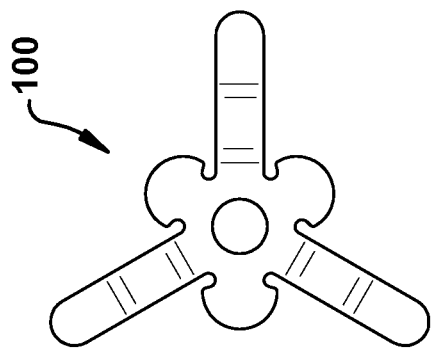
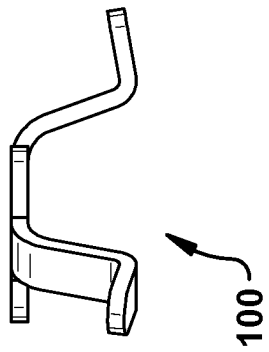
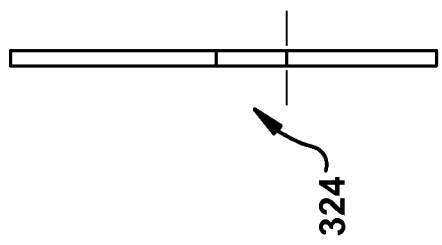
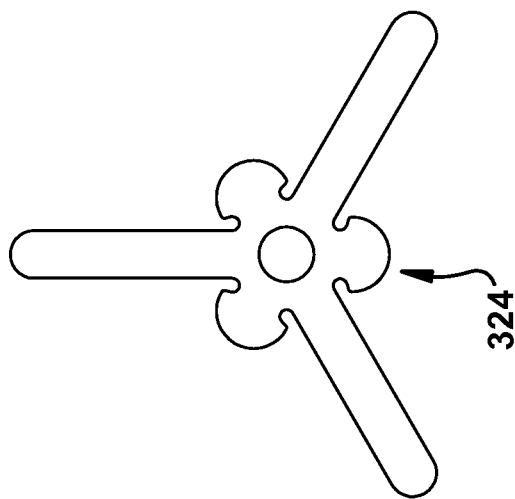

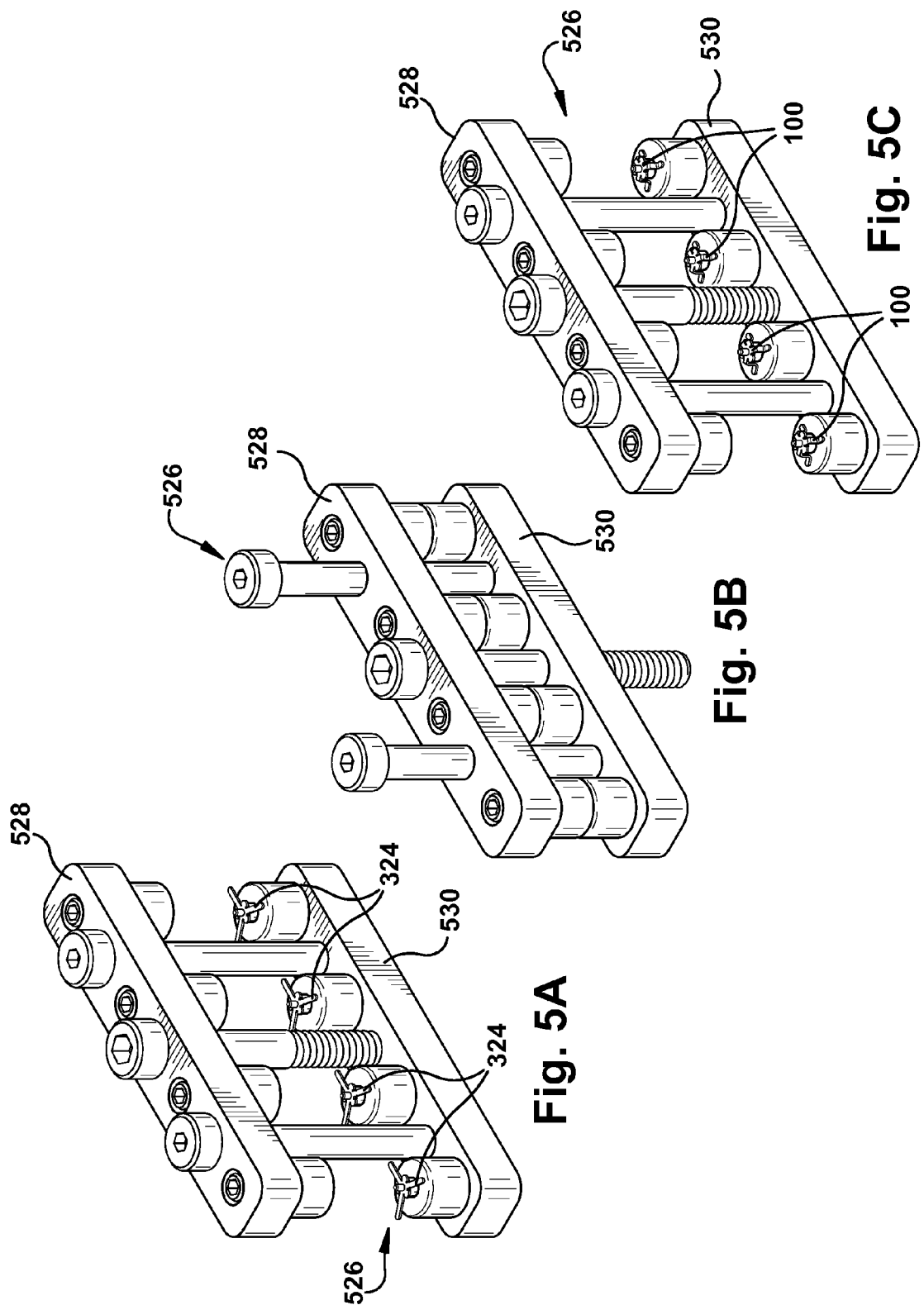

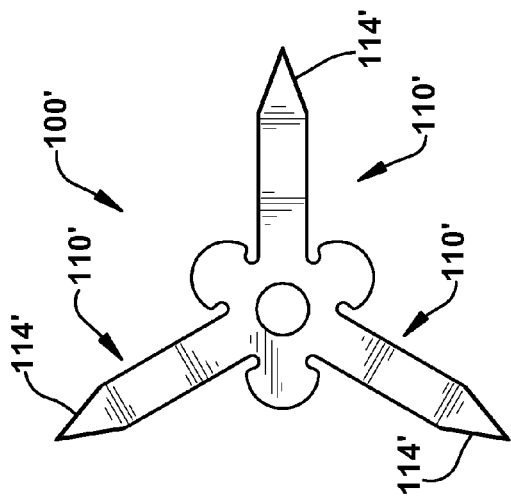
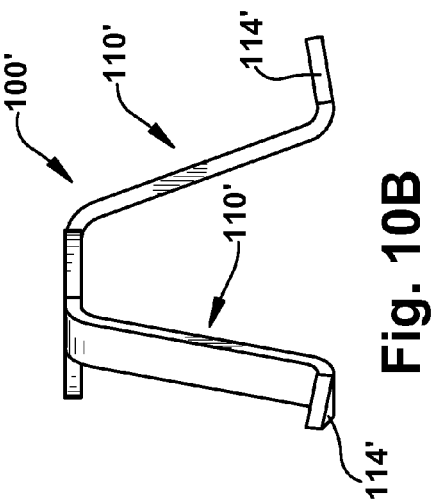
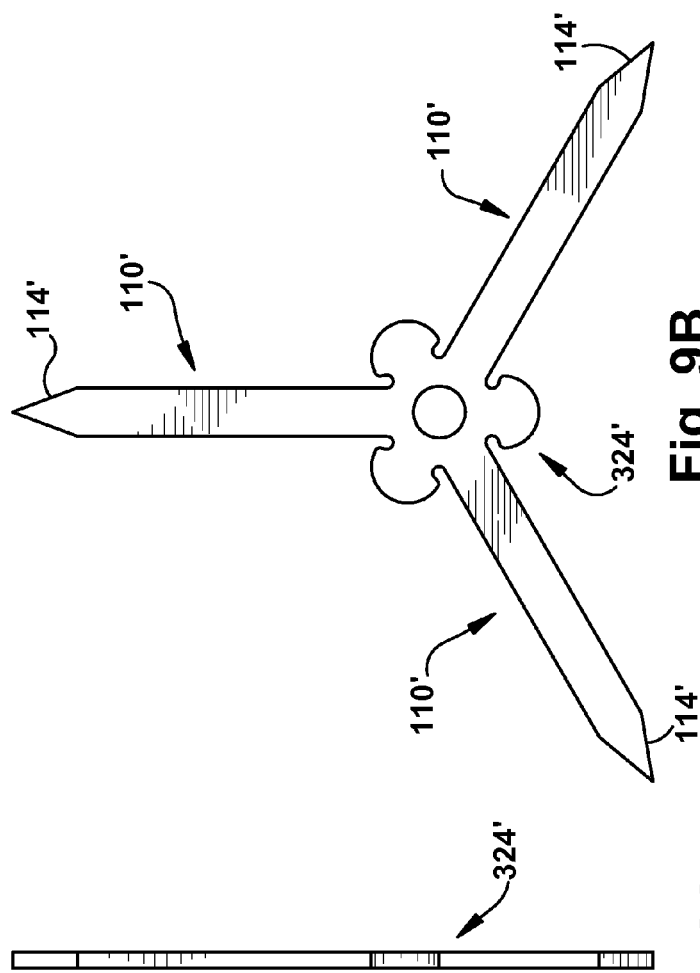

ENDOVASCULAR STAPLE CLIP AND STAPLER

RELATED APPLICATION

This application claims priority from U.S. Provisional Application No. 61/763,604, filed 12 Feb. 2013, the subject matter of which is incorporated herein by reference in its entirety.

TECHNICAL FIELD

The present invention relates to an apparatus and method for use of an endovascular staple clip and stapler and, more particularly, to endovascular stapling devices and methods for use in the fixation of grafts to the walls of vessels.

BACKGROUND OF THE INVENTION

In modern medical practice, it is sometimes desirable to pass a staple clip or other type of clip into or through the wall of a luminal anatomical structure (e.g., a blood vessel or other anatomical conduit) for the purpose of attaching an article (e.g., an endoluminal, extraluminal, or transluminal graft) or other apparatus to the wall of the anatomical structure.

Examples of medical procedures wherein it may be desirable to anchor or attach a graft or other apparatus to the wall of a blood vessel or other luminal anatomical conduit include certain endovascular grafting procedures whereby a tubular graft is placed within the lumen of an aneurysmic blood vessel to create a neo-lumen or artificial flow conduit through an aneurism, thereby eliminating the exertion of blood pressure on the aneurism and allowing the aneurysmic space to subsequently become filled in with granulation tissue. These endovascular grafting procedures have heretofore been used to treat aneurisms of the abdominal aorta, as well as aneurisms of the descending thoracic aorta. The endovascular grafts typically incorporate or are combined with one or more radially expandable stents which are radially expanded in situ to anchor the tubular graft to the wall of the blood vessel at sites upstream and downstream of the aneurism. Thus, the grafts are typically held in place by friction via the self-expanding or balloon expandable stents. The grafts may also be affixed to vessels with hooks or barbs.

However, in the event that these stent(s) fail to establish sound frictional engagement with the blood vessel wall, the graft may undergo undesirable migration or slippage, or blood may leak into the aneurysmic sac, sometimes referred to as an "endoleak". Thus, in view of the above-mentioned undesirable complications associated with the use of radially expandable stents to frictionally anchor a graft or other apparatus to the wall of a blood vessel or other luminal anatomical structure, there exists a need for the development of new endoluminal attachment devices which may be used to deliver one or more staple clips to a patient tissue. In this regard, while surgical stapling devices are generally known, the anatomical constraints presented by endovascular application (e.g., catheter-based) present numerous staple/clip deployment difficulties.

SUMMARY OF THE INVENTION

In an embodiment of the present invention, a staple clip for providing an attachment function in a surgical procedure is described. A center hub has a center hub aperture. The center hub defines a lateral hub plane. A plurality of joining legs each has an inner leg end attached to the center hub and an outer foot defining a lateral foot plane. The inner leg end and outer foot are separated along the leg by an elongate leg body extending laterally outward and longitudinally downward from the center hub. A plurality of lobe pads are attached to the center hub and lie substantially within the lateral hub plane. The inner leg ends and lobe pads alternate with each other around a periphery of the center hub.

In an embodiment of the present invention, a method of providing an attachment function in a surgical procedure is provided. A clip is provided. A center hub of the clip has a center hub aperture. The center hub defines a lateral hub plane. A plurality of joining legs are provided, each having an inner leg end attached to the center hub and an outer foot defining a lateral foot plane. The inner leg end and outer foot are separated along the leg by an elongate leg body extending laterally outward and longitudinally downward from the center hub. The staple clip is inserted through a thickness of each of a stack of a plurality of planar structures to be joined such that the center hub is on an outward-facing surface of an outermost planar structure, the joining legs extend through the thickness of all of the planar structures, and the outer feet are located adjacent an outward-facing surface of the innermost planar structure.

BRIEF DESCRIPTION OF THE DRAWINGS

For a better understanding of the invention, reference may be made to the accompanying drawings (which are not drawn to scale unless otherwise stated herein), in which:

FIGS. 3A and 3B are side and top views, respectively, of the embodiment of FIG. 1A in an intermediate process form;

FIGS. 4A and 4B are side and top views, respectively, of the embodiment of FIG. 1A in a final form;

FIGS. 5A, 5B, and 5C are schematic views depicting a portion of a manufacturing process of the embodiment of FIG. 1A;

FIGS. 9A and 9B are side and top views, respectively, of an embodiment of the present invention in an intermediate process form;

FIGS. 10A and 10B are side and top views, respectively, of the embodiment of FIGS. 9A and 9B in a final form.

DESCRIPTION OF EMBODIMENTS

Figure 1A:
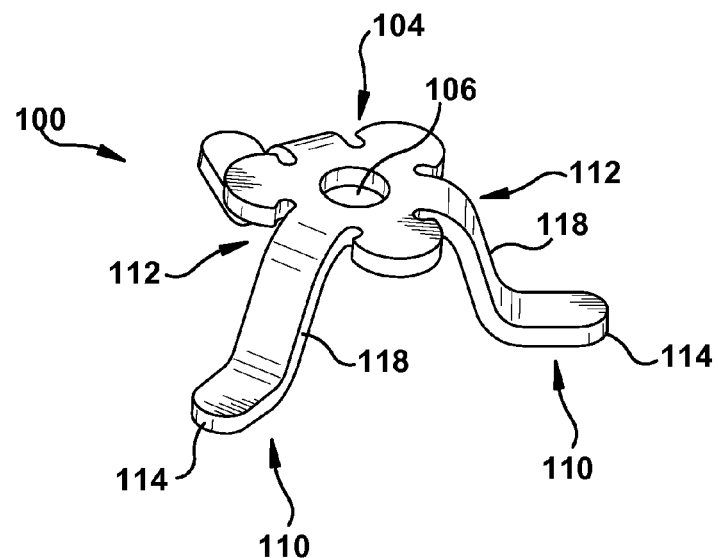
FIG. 1A is a side perspective view of one embodiment of the present invention.
Figure 1B:
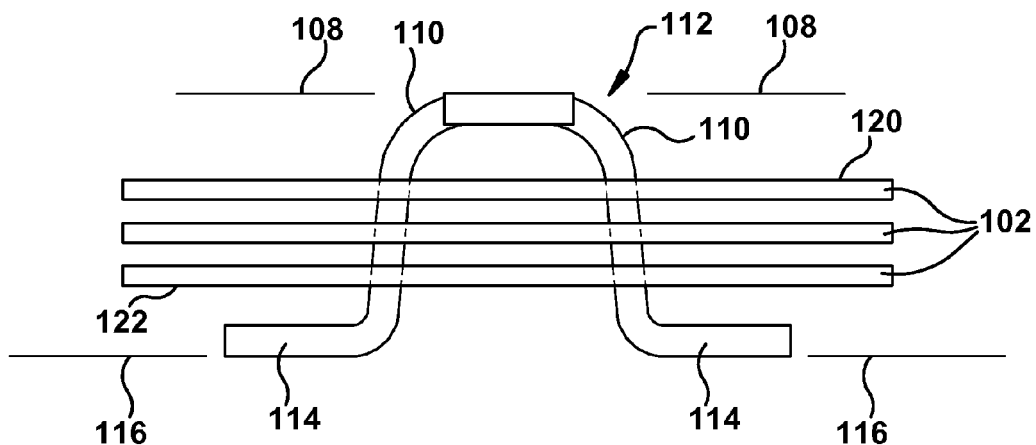
FIG. 1B is a schematic side view of the embodiment of FIG. 1A in an example use environment.

In accordance with the present invention, FIGS. 1A and 1B depict a staple clip 100. The clip 100 may be used to help provide an attachment between two or more planar structures 102, which will be described herein as being patient tissues in a surgical environment, but which can be any natural or artificial sheets of material which are desired to be attached together in a stacked manner. In the orientation of FIG. 1B, the planar structures 102 are substantially larger in a direction into and out of the page of the Figures than within the page—that is, the view of FIG. 1B is a "slice" through the thickness of the stack of planar structures. It is contemplated that any suitable materials may be attached together using the clip 100 of the present invention, whether or not they are planar (locally or globally), in much the same manner as office staples are used to hold together stacks of paper.

The clip 100 includes a center hub 104 having a center hub aperture 106, the center hub defining a lateral hub plane 108 which, in the orientation of FIG. 1B, is into and out of the plane of the page, and thus is represented as a line in FIG. 1B. At least one joining leg 110, a plurality of joining legs shown in the Figures, has an inner leg end 112 attached to the center hub 104. An outer foot 114 of each joining leg 110 defines a lateral foot plane 116 which, in the orientation of FIG. 1B, is into and out of the plane of the page, and thus is represented as a line in FIG. 1B. The lateral foot plane 116 and the lateral hub plane 108 may be substantially parallel for certain use environments of the present invention.

The inner leg end 112 and outer foot 114 of each joining leg 110 are separated along the leg by an elongate leg body 118, which may extend both laterally outward and longitudinally downward from the center hub 104, as shown in FIG. 1A. In embodiments having multiple joining legs 110, the joining legs may be evenly spaced around the periphery of the center hub 104 or may be unevenly spaced in any desired configuration.

At least one lobe pad 120, a plurality of lobe pads shown in the Figures, may be attached to the center hub 104 and lie substantially within the lateral hub plane 108. When there are multiple of each present, the inner leg ends 112 and lobe pads 120 may alternate with each other around a periphery of the center hub 104, as shown in FIG. 1A. The center hub 104 is shown in the Figures as being substantially circular in the depicted example embodiment, but may be any suitable shape. For example, the center hub 104 may be ovoid/elongate or any other circular, linear, and/or curvilinear shape, potentially having differing numbers of joining legs 110 on each side. The center hub 104 or any other structure of the clip 100 may be asymmetrical in any plane as desired. For example, at least one joining leg 110 of a single clip 100 could have a length of an elongate leg body 118 different from that of at least one other joining leg 110.

With reference to FIG. 1B, the clip 100 may be inserted through a thickness of each of a stack of a plurality of planar structures 102 to be joined such that the center hub 104 is on an outward-facing surface 120 of an outermost planar structure, the joining legs 110 extend through the thickness of all of the planar structures, and the outer feet 114 are located adjacent an outward-facing surface 122 of the innermost planar structure.

Figure 2:
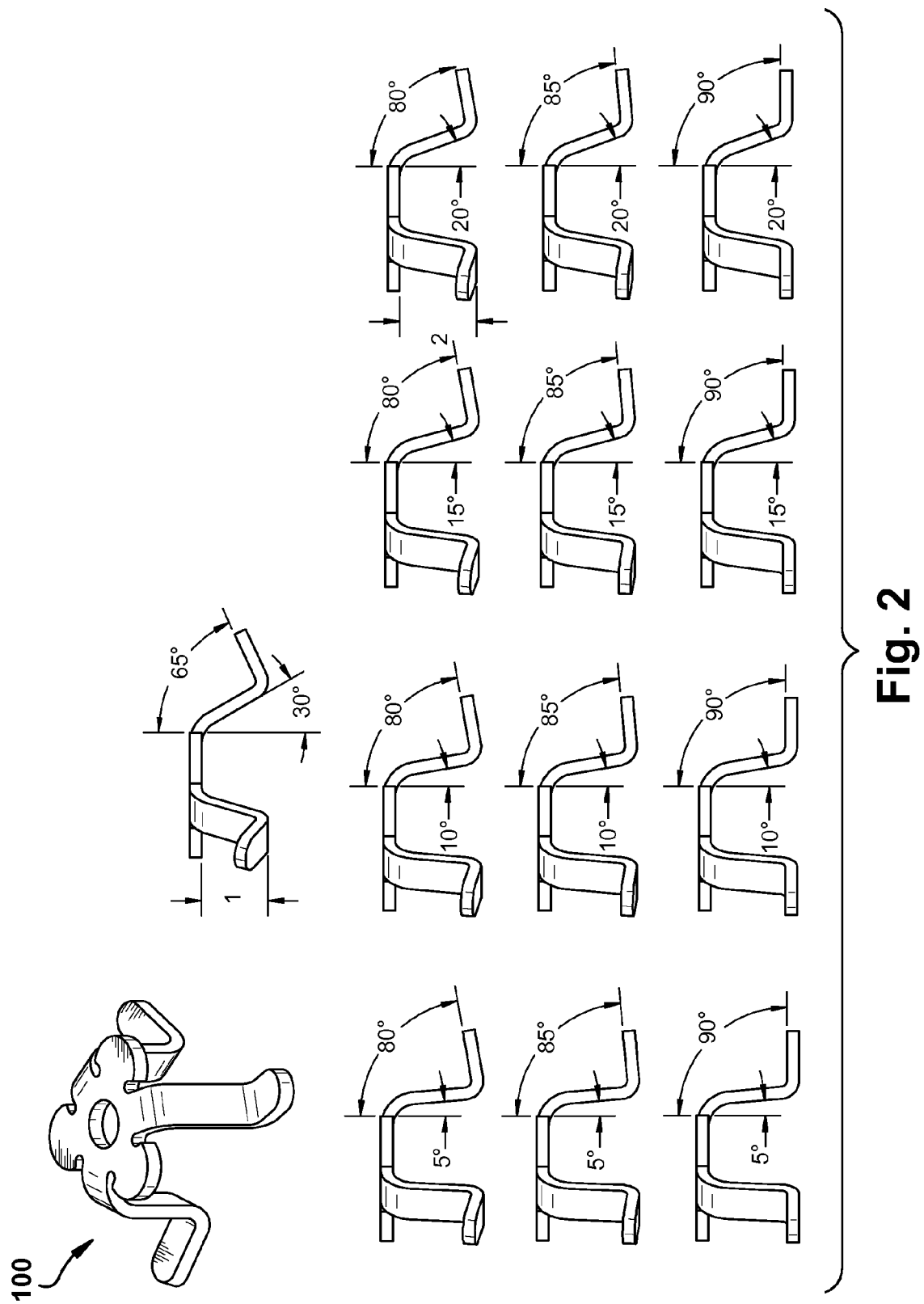
FIG. 2 is a schematic side view of an array of embodiments of FIG. 1A in different configurations.

FIG. 2 schematically depicts a plurality of clips 100 having a variety of angular configurations. One of ordinary skill in the art can readily choose one of these example configurations, or generate a clip 100 having any desirable configurations, for a particular application of the present invention.

FIGS. 3A and 3B schematically depict a flat "blank" 324 that can be fabricated, such as by stamping, laser-cutting, jigsawing, molding/casting, or any other desired method, as an intermediate step in the creation of the clip 100. For example, the blank 324 may be cut from a sheet of Nitinol or any other desired material. The finished clip 100 is shown in FIGS. 4A and 4B.

FIGS. 5A, 5B, and 5C depict a sequence by which the blanks 324 as shown in FIGS. 3A and 3B may be pressed into the clips 100 of FIGS. 4A and 4B. In FIGS. 5A, 5B, and 5C, a press 526 includes an upper press plate 528 and a lower press plate 530. The blanks 324 are placed in between the upper and lower press plates 528 and 530 (at least one of which includes a die or other shaping surface), as shown in FIG. 5A. As depicted in FIG. 5B, the press 526 is closed at a suitable pressure, for a suitable length of time, to cause the blanks 324 to assume the final clip 100 shape. When the blanks 324 are made from Nitinol or another shape-memory material, the press 526 may include temperature change or other means for "setting" the shape-memory material in a desired manner. The press 526 is opened, as shown in FIG. 5C with the completed clips 100 ready for removal from the press, finishing using any suitable treatments, and storage and/or deployment.

Figure 6:
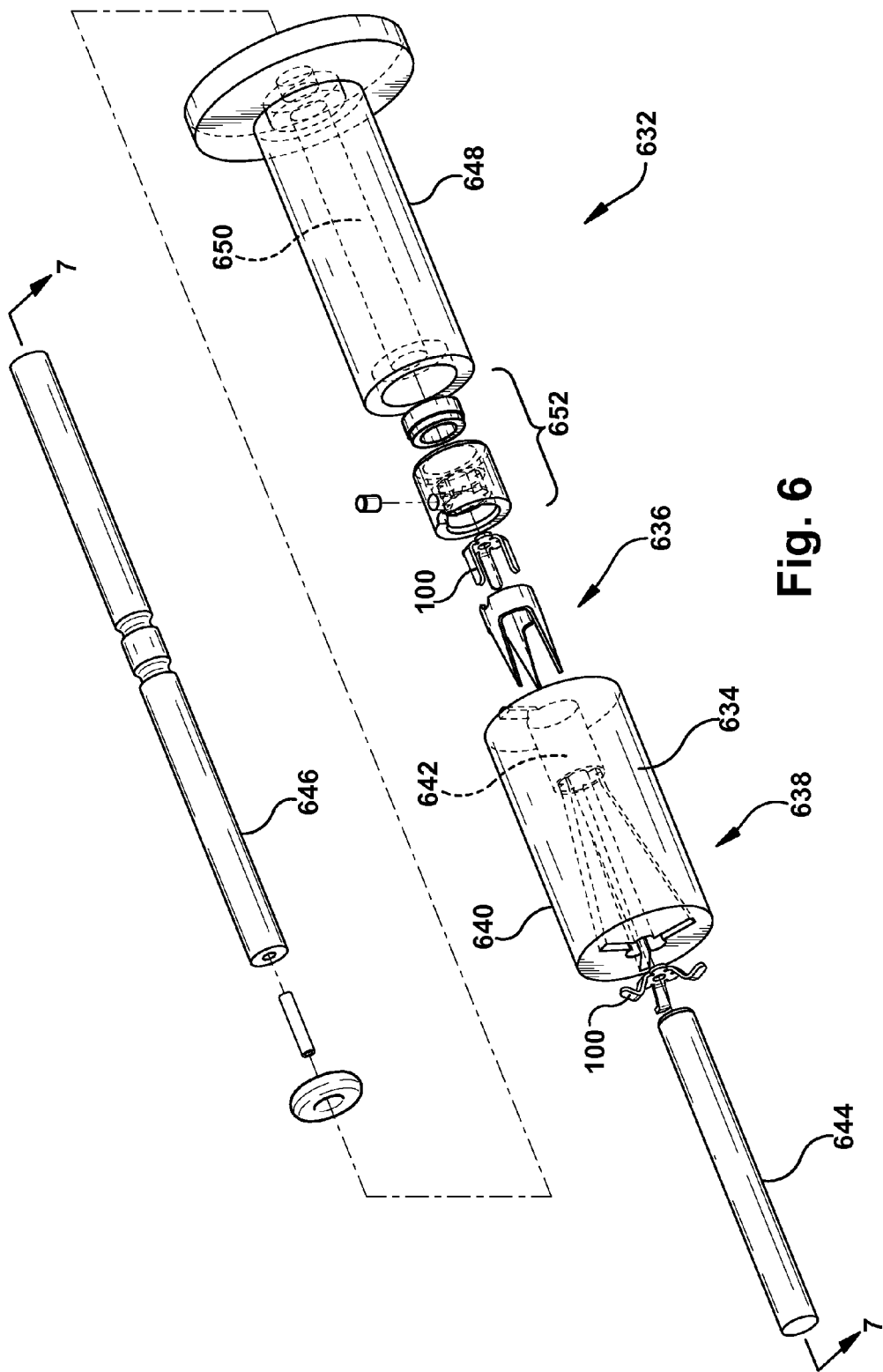
FIG. 6 is an exploded view of a tool for use with the embodiment of FIG. 1A.

FIG. 6 depicts an exploded view of a stapler 632 which may be used to deploy at least one clip 100 at a desired deployment site. A load tool 634 has proximal and distal tool ends 636 and 638, respectively, longitudinally spaced apart by a tool body 640. A central tool lumen 642 extends completely through the tool body 640 between the proximal and distal tool ends 636 and 638. The central tool lumen 642 is configured to allow passage therethrough of at least one clip 100. Optionally, the stapler 632 may be capable of deploying a plurality of clips 100 in sequence without having to be removed from the deployment site and reloaded.

A load plunger 644 may be removably located within at least a portion of the central tool lumen 642. The load plunger 644 is configured for longitudinal motion in and out of the central tool lumen 642 from the distal tool end 638. The load plunger 644 may be removed completely from the stapler 632 when not being used to load clip(s) 100 into the stapler.

A deployment plunger 646 may be removably located within at least a portion of the central tool lumen 642. The deployment plunger 646 is configured for longitudinal motion in and out of the central tool lumen 642 from the proximal tool end 636. A plunger housing 648 is located adjacent the proximal tool end 636. The plunger housing 648 supports the deployment plunger 646 for longitudinal movement relative thereto.

The central tool lumen 642 may extend coaxially with, and longitudinally adjacent to, a central plunger lumen 650 of the deployment plunger 646. A guidewire (not shown) may be inserted through the central tool and plunger lumens 642 and 650 to guide the stapler 632 to a desired deployment site within the patient's body in a known manner.

A clip retainer 652 is interposed longitudinally between the load tool 634 and the plunger housing 648 and is configured to selectively retain a clip 100 for movement to a desired deployment site.

Figure 7:
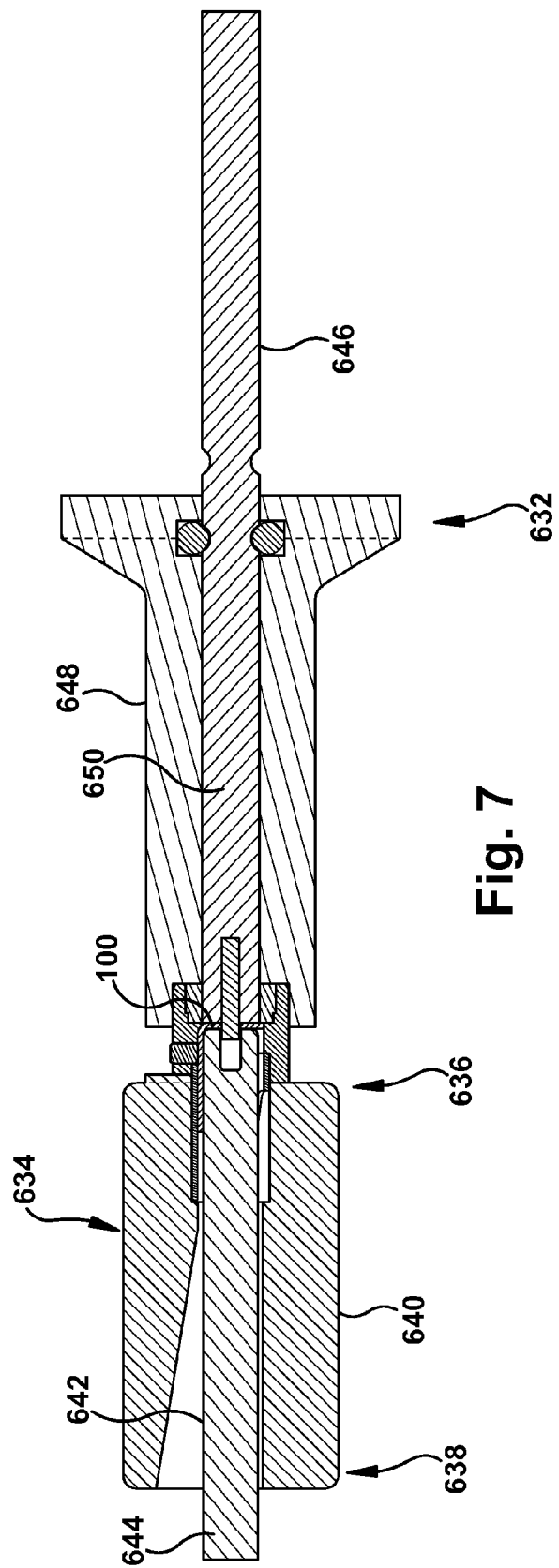
FIG. 7 is a sectional assembled view taken along line 7-7 of FIG. 6.

FIG. 7 is a cross-sectional assembled view taken along line 7-7 of FIG. 6. In FIG. 7, the load plunger 644 is pushing a clip 100 into a "ready to use" position within the load tool 634. As is shown in FIG. 7, the central tool lumen 642 has an angled cross-section, which is used to gradually straighten out at least one originally bent joining leg 110 as the clip 100 is pushed proximally (toward the right, in the orientation of FIG. 7) into the load tool 634.

Figure 8A:
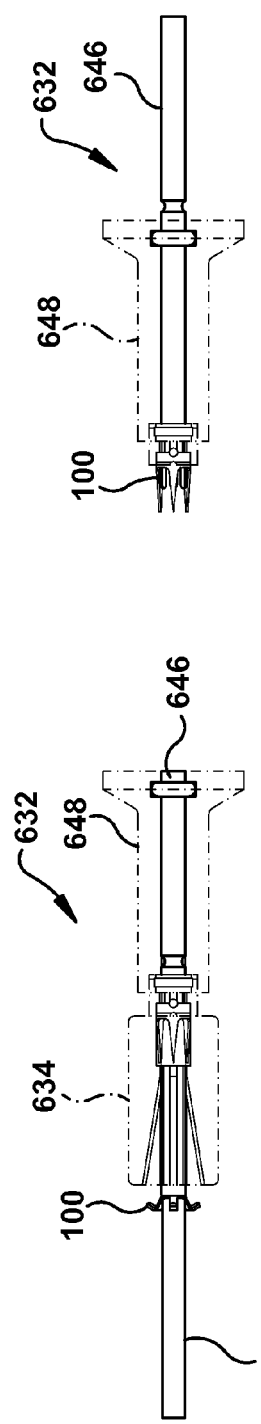
FIGS. 8A-8F are schematic partial side views of a sequence of use of the tool of FIG. 6.
Figure 8B:
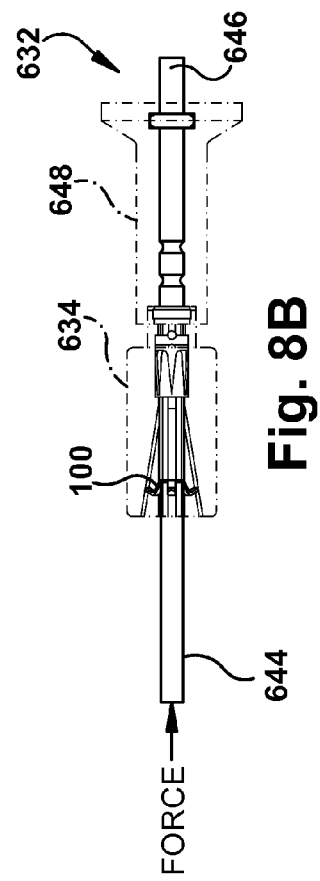
Figure 8C:
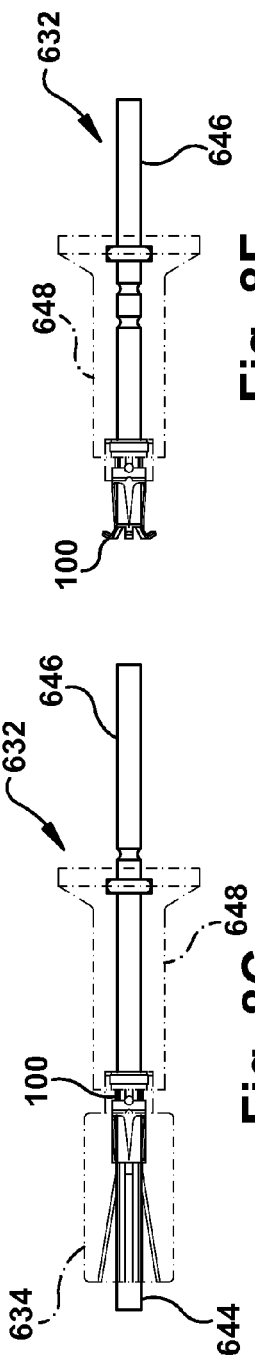
Figure 8D:
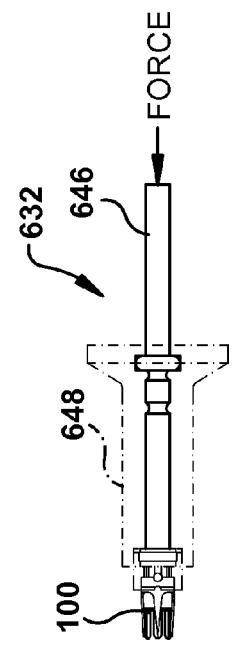
Figure 8E:
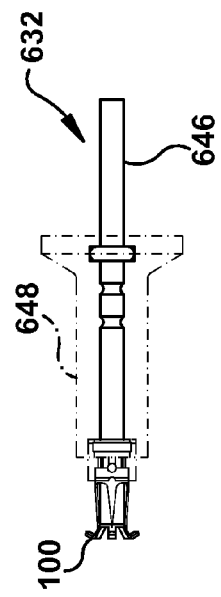

FIGS. 8A-8F depict a sequence of operation of the stapler 632. A clip 100 is placed into the distal tool end 638, and the load plunger 644 is placed into the distal tool end longitudinally distally adjacent the clip in FIG. 8A. The load plunger 644 is moved proximally to urge the clip 100 through the central tool lumen 642 and into retained engagement with the clip retainer 652, as shown in FIGS. 8B-8C. The load plunger 644 and load tool 634 are removed, leaving the configuration shown in FIG. 8D. The clip retainer 652 is placed longitudinally adjacent a desired deployment site, and, as shown in FIG. 8E, the deployment plunger 646 is moved longitudinally proximally within the central plunger lumen 650 to urge the clip 100 distally out of the clip retainer and into engagement with a desired target structure (e.g., at least one planar structure 102) at the deployment site. For example, structures of the stapler 632, ambient temperatures, or any other suitable mechanism/factor could be used to maintain a "straightened" configuration of the joining legs 110 as those joining legs are pushed through apertures (not shown) in at least one planar structure 102. The apertures may be existing (e.g., "precut") or could be created and/or enlarged via action of the joining legs 110 being pushed into the planar structure 102.

Figure 8F:
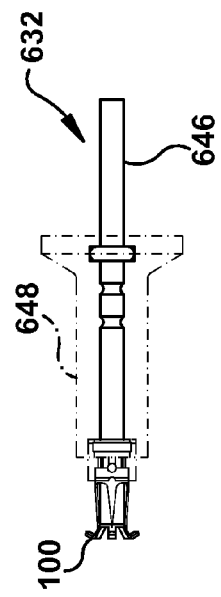

Optionally, one or more substantially "straightened" joining legs 110 of a clip 100 could be pushed sequentially through apertures (created in any suitable manner before and/or during passage therethrough of the joining leg) in multiple, stacked planar structures 102, in much the same manner as a paper brad engages multiple ones of a stack of papers. The joining legs 110, extending through the thickness(es) of the planar structure(s) 102, will then regain the bent configuration as shown in FIG. 8F. The resulting "joined stack" will resemble the schematic view of FIG. 1B.

The deployed clip 100 may be released from the stapler 632 once the arrangement/configuration of FIG. 8F has been reached. Optionally, magnetic, adhesive, interference-fit, or other suitable urging means could be used to hold, or assist with holding, the clips 100 in a desired relationship with structures of the stapler 632 before, during, and/or after engagement of the clip(s) with one or more planar structures 102.

FIGS. 9A-10B illustrate a second embodiment of a clip 100'. The clip 100' of FIGS. 9A-10B is similar to the clip 100 of FIGS. 1-8F and therefore, structures of FIGS. 9A-10B that are the same as or similar to those described with reference to FIGS. 1-8F have the same reference numbers with the addition of a "prime" mark. Description of common elements and operation similar to those in the previously described first embodiment will not be repeated with respect to the second embodiment FIGS. 9A and 9B schematically depict a flat "blank" 324' that can be fabricated, such as by stamping, laser-cutting, jigsawing, molding/casting, or any other desired method, as an intermediate step in the creation of the clip 100'. For example, the blank 324' may be cut from a sheet of Nitinol or any other desired material. The finished clip 100' is shown in FIGS. 10A and 10B.

As can be seen in FIGS. 9A-10B, the outer foot 114' of each joining leg 110' of the second embodiment has a pointed and/or sharpened tip, as opposed to the substantially rounded outer foot 114 of the first embodiment. This pointed outer foot 114' may be helpful in piercing through a planar structure 102 which does not already have an aperture therethrough to admit the joining leg 110'. As with any structure of the present invention, the outer feet 114' could have any configuration (e.g., pointed, rounded, convex in any plane, concave in any plane, pierced, or any other physical characteristic) desirable for a particular use environment.

While aspects of the present invention have been particularly shown and described with reference to the preferred embodiment above, it will be understood by those of ordinary skill in the art that various additional embodiments may be contemplated without departing from the spirit and scope of the present invention. For example, the specific methods described above for using the clip 100 are merely illustrative; one of ordinary skill in the art could readily determine any number of tools, sequences of steps, or other means/options for placing the above-described apparatus, or components thereof, into positions substantively similar to those shown and described herein. Any of the described structures and components could be integrally formed as a single piece or made up of separate sub-components, with either of these formations involving any suitable stock or bespoke components and/or any suitable material or combinations of materials; however, the chosen material(s) should be biocompatible for many applications of the present invention. Though certain components described herein are shown as having specific geometric shapes, all structures of the present invention may have any suitable shapes, sizes, configurations, relative relationships, cross-sectional areas, or any other physical characteristics as desirable for a particular application of the present invention. The stapler 632 may include a plurality of structures cooperatively forming any components thereof and temporarily or permanently attached together in such a manner as to permit relative motion (e.g., pivoting, sliding, or any other motion) therebetween as desired. Any structures or features described with reference to one embodiment or configuration of the present invention could be provided, singly or in combination with other structures or features, to any other embodiment or configuration, as it would be impractical to describe each of the embodiments and configurations discussed herein as having all of the options discussed with respect to all of the other embodiments and configurations. A device or method incorporating any of these features should be understood to fall under the scope of the present invention as determined based upon the claims below and any equivalents thereof.

Other aspects, objects, and advantages of the present invention can be obtained from a study of the drawings, the disclosure, and the appended claims.

We claim:

1. A method of providing an attachment function in a surgical procedure, the method comprising the steps of:
   providing a clip including
     a center hub having a center hub aperture, the center hub defining a lateral hub plane, and
     a plurality of joining legs, each having an inner leg end attached to the center hub and an outer foot defining a lateral foot plane, the inner leg end and outer foot being separated along the leg by an elongate leg body extending laterally outward and longitudinally downward from the center hub;
   inserting the staple clip through a thickness of each of a stack of a plurality of planar structures to be joined such that the center hub is on an outward-facing surface of an outermost planar structure, the joining legs extend through the thickness of all of the planar structures, and the outer feet are located adjacent an outward-facing surface of the innermost planar structure;
   providing a stapler for deploying the staple clip, the stapler comprising
     a load tool having proximal and distal tool ends longitudinally spaced apart by a tool body, a central tool lumen extending completely through the tool body between the proximal and distal tool ends, the central tool lumen being configured to allow passage of at least one staple clip,
     a load plunger removably located within at least a portion of the central tool lumen, the load plunger being configured for longitudinal motion in and out of the central tool lumen from the distal tool end, a deployment plunger removably located within at least a portion of the central tool lumen, the deployment plunger being configured for longitudinal motion in and out of the central tool lumen from the proximal tool end, a plunger housing located adjacent the proximal tool end, the plunger housing supporting the deployment plunger, and a clip retainer interposed longitudinally between the load tool and the plunger housing; and placing a staple clip into the distal tool end;

placing the load plunger into the distal tool end longitudinally distally adjacent the staple clip;

moving the load plunger proximally to urge the staple clip through the central tool lumen and into retained engagement with the clip retainer;

removing the load plunger and load tool;

placing the clip retainer longitudinally adjacent a desired deployment site; and moving the deployment plunger longitudinally proximally within the central tool lumen to urge the staple clip distally out of the clip retainer and into engagement with a desired target structure at the deployment site.

2. The method of claim 1, including the step of inserting a guidewire through the central plunger lumen to guide the stapler to a desired deployment site within the patient's body.

* * * * *